(12) United States Patent
Schmitt et al.

(10) Patent No.: US 9,047,702 B2
(45) Date of Patent: Jun. 2, 2015

(54) COMPUTED TOMOGRAPHY SYSTEM AND METHOD FOR TRACKING A BOLUS

(75) Inventors: Holger Schmitt, Hamburg (DE); Michael Grass, Buchholz in der Nordheide (DE)

(73) Assignee: Koninklijke Philips N.V., Eindhoven (NL)

( * ) Notice: Subject to any disclaimer, the term of this patent is extended or adjusted under 35 U.S.C. 154(b) by 136 days.

(21) Appl. No.: 13/977,042

(22) PCT Filed: Jan. 4, 2012

(86) PCT No.: PCT/IB2012/050042
§ 371 (c)(1),
(2), (4) Date: Jun. 28, 2013

(87) PCT Pub. No.: WO2012/093364
PCT Pub. Date: Jul. 12, 2012

(65) Prior Publication Data
US 2013/0279783 A1    Oct. 24, 2013

(30) Foreign Application Priority Data
Jan. 6, 2011   (EP) .................................... 11150301

(51) Int. Cl.
*G06K 9/00* (2006.01)
*G06T 11/00* (2006.01)
*A61B 6/03* (2006.01)
*A61B 6/00* (2006.01)

(52) U.S. Cl.
CPC ............... *G06T 11/008* (2013.01); *A61B 6/032* (2013.01); *A61B 6/469* (2013.01); *A61B 6/481* (2013.01); *A61B 6/488* (2013.01); *A61B 6/504* (2013.01)

(58) Field of Classification Search
None
See application file for complete search history.

(56) References Cited

U.S. PATENT DOCUMENTS

| 6,272,200 B1 * | 8/2001 | Pan et al. ......................... 378/15 |
| 7,054,406 B2 | 5/2006 | Ikeda et al. |
| 2003/0108149 A1 | 6/2003 | Tsuyuki |

(Continued)

FOREIGN PATENT DOCUMENTS

| EP | 2087843 A1 | 8/2009 |
| WO | 2010111457 A1 | 9/2010 |

*Primary Examiner* — Nancy Bitar

(57) ABSTRACT

The present invention relates to a computed tomography system (10) and a corresponding method which enable tracking of a contrast material bolus and which involve a reduced radiation dose. The proposed computed tomography system (10) comprises an acquisition unit including an X-ray source (18) and an X-ray detector (30) for acquiring projection data sets (42, 44, 46), a reconstruction unit (41) for reconstructing a planning image (48) from a first projection data set (42), an identification unit (52) for identifying a region of interest (40) in the planning image (48), a selection unit (54) for selecting a projection angle (60) through the region of interest (40), a calculator (62) for calculating a target projection value (64) for a projection of said region of interest (40) with the selected projection angle (60), a control unit (32) for controlling said acquisition unit to acquire a second, reduced projection data set (44) including projection data from projections of said region of interest (40) with the selected projection angle (60), and a comparator (68) for comparing projection values of the second projection data set (44) with the target projection value (64), wherein the control unit (32) is adapted to control the acquisition unit to initiate the acquisition of a third projection data set (46) based on the comparison result (70) and to reconstruct a diagnostic image (50) from the third projection data set (46).

15 Claims, 5 Drawing Sheets

(56) References Cited

U.S. PATENT DOCUMENTS

| | | | |
|---|---|---|---|
| 2003/0161435 A1* | 8/2003 | Ozaki | 378/4 |
| 2007/0062251 A1* | 3/2007 | Anex | 73/1.36 |
| 2007/0258558 A1 | 11/2007 | Nishide et al. | |
| 2008/0292045 A1* | 11/2008 | Iisaku et al. | 378/4 |
| 2008/0317310 A1* | 12/2008 | Suresh et al. | 382/130 |
| 2009/0252285 A1 | 10/2009 | Shapiro et al. | |
| 2010/0119034 A1* | 5/2010 | Hein et al. | 378/19 |
| 2010/0248582 A1* | 9/2010 | Tome | 446/82 |
| 2010/0249582 A1 | 9/2010 | Feuerlein et al. | |

* cited by examiner

COMPUTED TOMOGRAPHY SYSTEM AND METHOD FOR TRACKING A BOLUS

FIELD OF THE INVENTION

The present invention relates to a computed tomography (CT) system, in particular for tracking a bolus. The present invention is also related to a corresponding method, computer program and processor, in particular for use in such a CT system.

BACKGROUND OF THE INVENTION

Bolus tracking is a commonly used method in CT angiography for determining the time of arrival at an organ of inflowing contrast agent injected into a peripheral vein. This method of imaging is used primarily to produce images of arteries, such as the aorta, pulmonary artery, cerebral and carotid arteries.

Known bolus tracking methods acquire a thin image slab and update it regularly using multiple short scans. The image intensity in a user-defined area is monitored, and the diagnostic image acquisition is started when a pre-defined intensity value is reached, indicating that the bolus has arrived at the target region. This kind of method requires that a significant amount of X-ray dose is spent only to find out the correct starting time of the acquisition.

U.S. Pat. No. 7,054,406 suggests reducing the radiation dose by including in a computed tomography system an X-ray supply unit performing low-dose X-ray scans and high-dose X-ray scans for a patient in which a contrast medium has been injected. The collected X-ray projection data are reconstructed to generate image data for low-dose scans and high-dose scans. In the low-dose scans that precede the high-dose scans, plural images are obtained in succession, in which ROIs (regions of interest) are set in given positions. A CT value calculating unit calculates the CT values in the ROIs in succession, and the calculated CT values are displayed as a time-density curve. The operator observes the state in which the contrast medium flows into the ROIs, and determines the timing at which the high-dose X-ray scan is started.

Although U.S. Pat. No. 7,054,406 reduces the patient radiation dose compared to acquiring only normal (high-dose) X-ray scans, the presented system still involves a substantial radiation dose only for determining when the high-dose X-ray scan should be started. Therefore, there is a need for a bolus tracking device and method which involve a reduced radiation exposure for the patient.

SUMMARY OF THE INVENTION

It is an object of the present invention to provide a computed tomography system and method that can track a bolus and involve a reduced amount of radiation exposure for the patient. It is another object of the present invention to provide a corresponding processor and computer program.

In a first aspect of the present invention a computed tomography system is presented that comprises
- an acquisition unit including an X-ray source and an X-ray detector for acquiring projection data sets,
- a reconstruction unit for reconstructing a planning image from a first projection data set,
- an identification unit for identifying a region of interest in the planning image,
- a selection unit for selecting a projection angle through the region of interest,
- a calculator for calculating a target projection value for a projection of said region of interest with the selected projection angle,
- a control unit for controlling said acquisition unit to acquire a second, reduced projection data set including projection data from projections of said region of interest with the selected projection angle, and
- a comparator for comparing projection values of the second projection data set with the target projection value, wherein the control unit is adapted to control the acquisition unit to initiate the acquisition of a third projection data set based on the comparison result and to reconstruct a diagnostic image from the third projection data set.

In a further aspect of the present invention a corresponding method for tracking a bolus in a computed tomography system is presented that comprises the steps of
- acquiring a first projection data set and reconstructing a planning image from said first projection data set,
- identifying a region of interest in the planning image,
- selecting a projection angle through the region of interest,
- calculating a target projection value for a projection of the region of interest with the selected projection angle,
- acquiring a second, reduced projection data set including projection data from projections of said region of interest,
- comparing projection values of the second, reduced projection data set with the target projection value, and
- acquiring a third projection data set and reconstructing a diagnostic image from the third projection data set, wherein acquiring the third projection data set is initiated based on the comparison result.

In a further aspect of the present invention there is provided a processor for use in a computed tomography system configured to control the computed tomography system to carry out the steps of
- acquiring a first projection data set and reconstructing a planning image from said first projection data set,
- allowing a user to identify a region of interest in the planning image,
- allowing a user to select a projection angle through the region of interest,
- calculating a target projection value for a projection of the region of interest with the selected projection angle,
- acquiring a second, reduced projection data set including projection data from projections of said region of interest,
- comparing projection values of the second, reduced projection data set with the target projection value, and
- acquiring a third projection data set and reconstructing a diagnostic image from the third projection data set, wherein acquiring the third projection data set is initiated based on the comparison result.

In yet another aspect of the present invention, there is provided a computer program which comprises program code means for causing a computer to control a computed tomography system to perform the steps of the processor when said computer program is carried out on a computer.

Preferred embodiments of the invention are defined in the dependent claims. It shall be understood that the claimed method, processor, and computer program have similar and/or identical preferred embodiments as the claimed system and as defined in the dependent claims.

The present invention suggests acquiring only one thin image slab (i.e. the second projection data set) for scan planning and then to determine the time of bolus arrival only from single X-ray projections. Since modern X-ray acquisition units, such as grid-switched tubes, allow for the acquisition of single projections, it is not necessary to acquire many short scans. Instead, it is sufficient to acquire one overview image (i.e. the planning image from the first projection data set) and identify the region of interest (ROI) therein. The arrival of the bolus can then be tracked in a reduced set of projections (i.e. said second projection data set) that go through the ROI.

The reduced set of projections can be only one projection, i.e., correspond to the intensity (count rate) that is obtained in a single detector element of the detector (generally comprising a plurality of detector elements arranged in an array of rows and columns). Alternatively, it can also be a (weighted) sum of the intensities (count rates) obtained in several (preferably neighboring) detector elements.

The inventors realized that, in order to track the arrival of the bolus at the target area, in general the acquisition of a single projection through the target area (ROI) is sufficient and leads to a dramatic reduction in X-ray dose. For example, a known method would reconstruct 10 images from 10 short scans, which each involve 1500 projections, leading to an overall acquisition of 15000 projections. With the method according to the present invention, only one short scan (first projection data set) and 10 single projections (second projection data set) would be needed, resulting in 1500+10×1=1510 projections.

In a preferred embodiment, the second, reduced projection data set comprises only projection data from projections of said region of interest with the selected projection angle. This reduces the number of projections (and thus also reduces radiation dose) and at the same time optimizes the accuracy of the target tracking. Ideally, the selected projection angle is such that few other structures that might also have uptake of the contrast agent are also in the line of the projection.

In another preferred embodiment, the identification unit comprises a first user interface, which allows a user to identify the ROI in the planning image. Typically, the first user interface comprises a display for showing the reconstructed planning image and a user input, which allows a user to identify the ROI. The user input could, for instance, be a computer mouse, which allows drawing the region of interest in the image, or a touch screen. The user interface can require the ROI to have a certain shape, for example circular or spherical. Alternatively, the user can draw arbitrary shapes. Once the user has identified the ROI, the boundary of the ROI can be shown overlaid with the planning image. This allows the user to verify accurate positioning.

In a preferred embodiment, the selection unit comprises a second user interface which allows a user to select the projection angle through the region of interest. The second user interface can share elements with the first user interface, for example both may comprise the same display. The second user interface comprises a user input for identifying the projection angle. For example, the scroll wheel of a computer mouse could be used to rotate the projection on the display, corresponding to different projection angles. The second user interface ensures that the projection always goes through the ROI. Selecting the projection angle typically involves only one degree of freedom because the projection can be rotated only within the transaxial plane. In principle, it is however also possible that the second user interface allows the user to tilt the projection such that it is no longer embedded in a transaxial plane.

In another embodiment of the proposed system, the selection unit is adapted for automatically selecting a preferred projection angle and the display is adapted for displaying said preferred projection angle. Automatically selecting the projection angle allows for an improved clinical workflow. Typically, the projection angle will be chosen such that it goes through the target area but does not go through other organs or body tissues that could also have uptake of the contrast agent. An experienced physician knows which other areas outside the target will not have contrast agent uptake. In some cases, however, simple rules might be sufficient to determine a suitable projection. For example, there could be the assumption that certain tissues, which can easily be recognized in a CT image, such as bone (high radiodensity) or low density lung tissue will typically have no contrast agent uptake. In such cases, the selection unit could automatically choose a preferred projection angle and display it to the user. The experienced physician would then only need to confirm the selection.

In another embodiment, the selection unit is adapted for automatically selecting the projection angle. If the selection unit uses a sufficiently accurate algorithm for determining the projection angle, this allows for an even more improved workflow because no interaction with the user is generally required, except for the identification of the ROI for which interaction with the user is preferred (although also automatic selection methods of the ROI are possible, e.g. dependent on a user input of the desired organ to be imaged, e.g. by image processing and recognition means).

In another embodiment of the proposed system, the selection unit is adapted for selecting more than one projection angle and the second reduced projection data set includes projection data from projections of the identified region of interest with more than one selected projection angles. Using more than one projection angle is useful for example if no single projection can be found that does not go through other tissues that might also yield contrast agent uptake. Having more than one projection angle can also be useful if one projection alone yields a signal that is too noisy. The more than one projection angles can be contained in the same transaxial plane, or they can be tilted in different angles. The system could also select more than one projection angles if the projection angle that was chosen by the user does not exactly correspond to one line between the radiation source and a detector.

In another embodiment of the present invention, the acquisition unit is adapted to acquire the projection values of the second projection data set at subsequent times and the comparator is adapted for computing a rate of change of the projection values acquired at subsequent times. This has the advantage that the arrival of the bolus at the target is not based on a threshold of the absolute increase of the intensity in the target but instead is based on a relative change in the projection value, compared to previously acquired projection values. A refined embodiment could also combine the requirement of an absolute increase in the projection value compared to the projection value of the acquisition for the planning image and an increase of the projection values of the second projection data set acquired at one time point compared to a previous time point. This can yield a more accurate identification of the target arrival time.

In another embodiment, the acquisition unit is adapted to acquire the projection values of the second projection data set at subsequent times with equal time intervals in between. The time intervals can be chosen based on the used contrast agent and the expected arrival time at the target.

In another preferred embodiment, the acquisition unit further comprises a dynamic collimator for narrowing the X-ray beam emitted from the X-ray source when the second projection data set is acquired. This has the advantage that the radiation beam is limited only to the selected projection line, which further reduces the radiation dose for the patient. Furthermore, a thin X-ray beam can be more precisely positioned to go through the ROI, even if the ROI is very small.

In yet another embodiment, the acquisition unit is adapted to acquire the second projection data set using a grid-switched X-ray source. Grid-switched tubes allow for the acquisition of single projection angles instead of angular segments, even though the ring, which comprises radiation source and detector unit, is continuously rotating at high speed during the acquisition.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
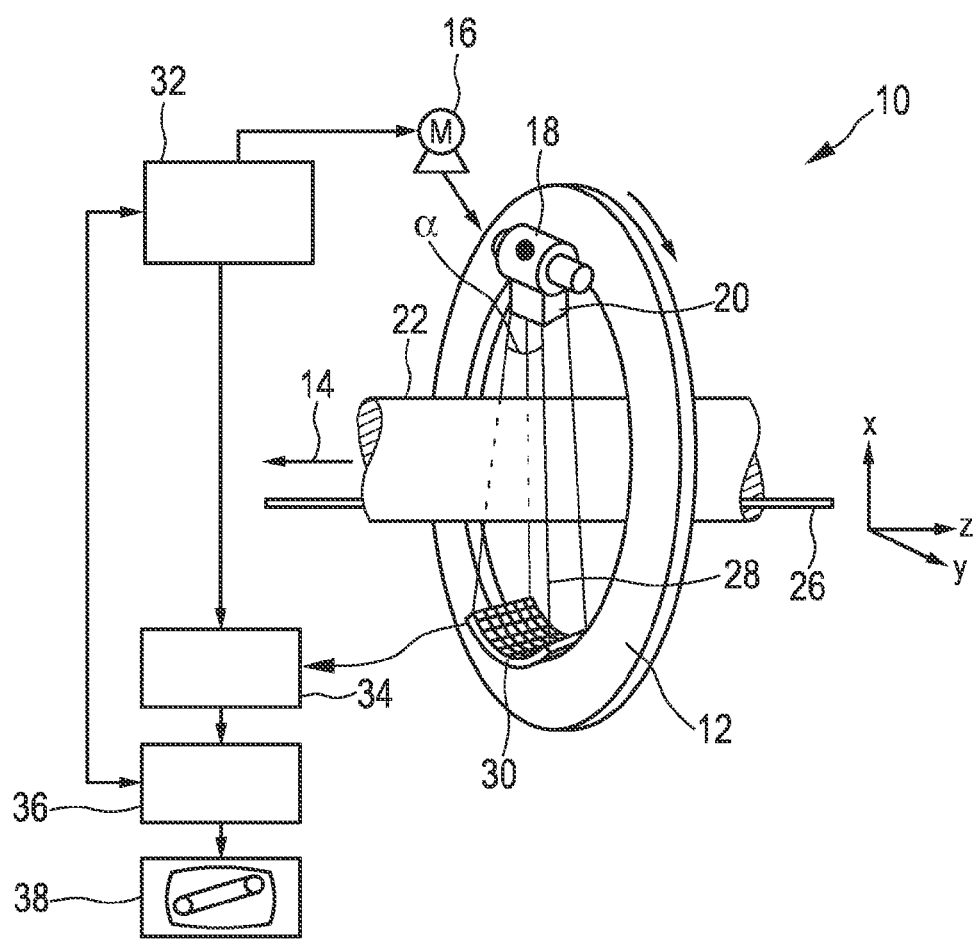
FIG. 1 shows a schematic perspective view of a computed tomography system in accordance with the present invention.
Figure 2A:
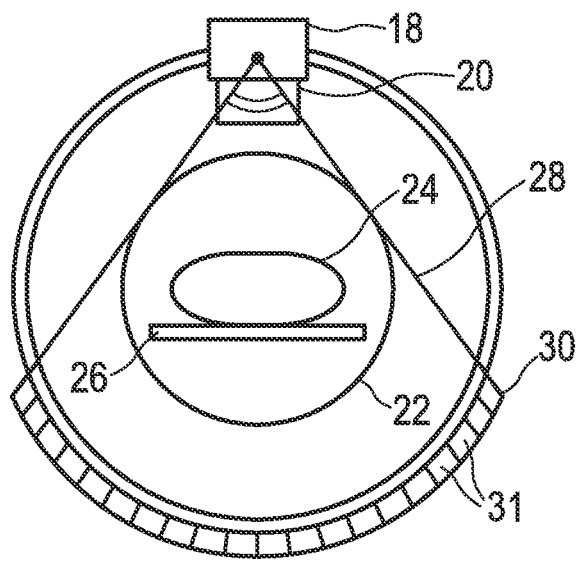
FIG. 2A and FIG. 2B show cross-sectional views of such a computed tomography system.
Figure 2B:
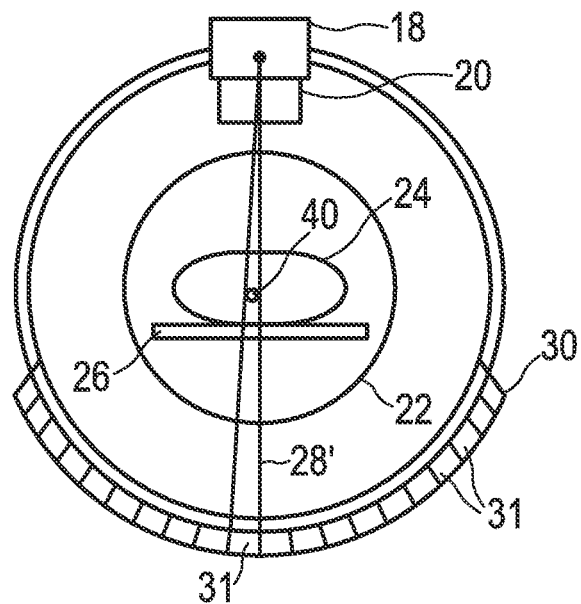

The computed tomography system 10 shown in FIGS. 1, 2A, and 2B includes a gantry 12 which is capable of rotation about an axis of rotation 14 which extends parallel to the z direction of the system of co-ordinates shown in FIG. 1 (and perpendicular to the plane of drawing of FIGS. 2A and 2B). To this end, the gantry is driven at a preferably constant, but adjustable speed by a motor 16. On the gantry there is mounted a radiation source 18, for example an X-ray source. This X-ray source is connected to a collimator arrangement 20 which, utilizing inter alia a diaphragm arrangement, forms a conical radiation beam 28 from the radiation produced by the radiation source 18, that is, a radiation beam 28 having a finite dimension other than zero in the direction of the z axis as well as in a direction perpendicular thereto (that is, in a plane perpendicular to the axis of rotation 14).

The radiation beam irradiates an examination zone 22 in which an object 24, for example a patient, arranged on a table top 26 of a patient table (not shown), may be situated. The examination zone 22 is shaped as a cylinder whose diameter is determined by the angle of aperture a of the radiation beam 28 (the angle of aperture is to be understood to mean the angle enclosed by a ray of the radiation beam 28 which is situated at the edge in a plane perpendicular to the axis of rotation 14 relative to the plane defined by the radiation source S and the axis of rotation).

After having traversed the examination zone 22, the X-ray beam 28 is incident on a two-dimensional detector 30 which is attached to the gantry 12 and comprises a plurality of detector rows, each of which comprises a plurality of detector elements 31. The detector rows are arranged in planes which are perpendicular to the axis of rotation 14, preferably on an arc of a circle around the radiation source 18. However, they may also be formed in a different way; for example, they may describe an arc of a circle around the axis of rotation 14 or be rectilinear. Each detector element 31 that is struck by the radiation beam 28 supplies a measuring value for a ray of the radiation beam 28 in each position of the radiation source 18. Sets of such measuring values will also be referred to as projection data sets hereinafter. A projection data set comprises measuring values acquired by one or more detector elements 31 at one or more projection angles.

The X-ray source 18 and the detector 30 together form an acquisition unit. The detector 18 generally also includes means for storing the acquired projection data. Such storage means may be included in the detector 30 or are (preferably) provided as an external separate storage unit 34 as shown in FIG. 1.

The examination zone 22, or the table top 26, can be displaced parallel to the axis of rotation 14, or parallel to the z axis, by means of a motor (not shown). The height of the table top 26 can be adjusted by means of another motor (not shown).

FIG. 2A shows a preferred embodiment of the proposed CT system in which the acquisition unit is used for acquiring a first and third projection data set. The collimator arrangement 20 is set such that the radiation beam 28 reaches all detector elements of the detector 30.

FIG. 2B shows the same CT system in which the collimator arrangement 20 is set such that it narrows the radiation beam 28' with the effect that it reaches only one detector element 31 of the detector 30. It is also set such that the ROI 40 is, at least partially, within the radiation beam 28'. The collimator arrangement 20 is dynamic, which means that it can quickly change between broad and narrow radiation beam 28. The second, reduced projection data set can therefore be acquired quickly after the acquisition of the first projection data set.

In alternative embodiments, however, the CT system does not use such a switchable collimator arrangement, but the collimator has a fixed setting (or no collimator is used at all) so that all projection data sets are generally acquired by a radiation beam 28 as shown in FIG. 2A.

For processing the various projection data sets acquired by the acquisition unit a processing unit 36 is provided. The processing by said processing unit 36 will be explained in detail below. Reconstructed images or image portions are displayed on a display unit 38.

Figure 3:
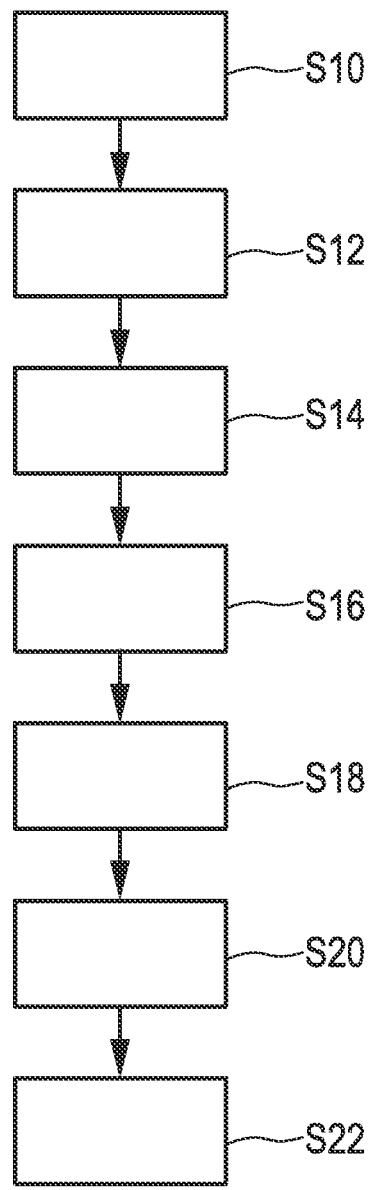
FIG. 3 shows a flow-chart of a method according to the present invention.
Figure 4:
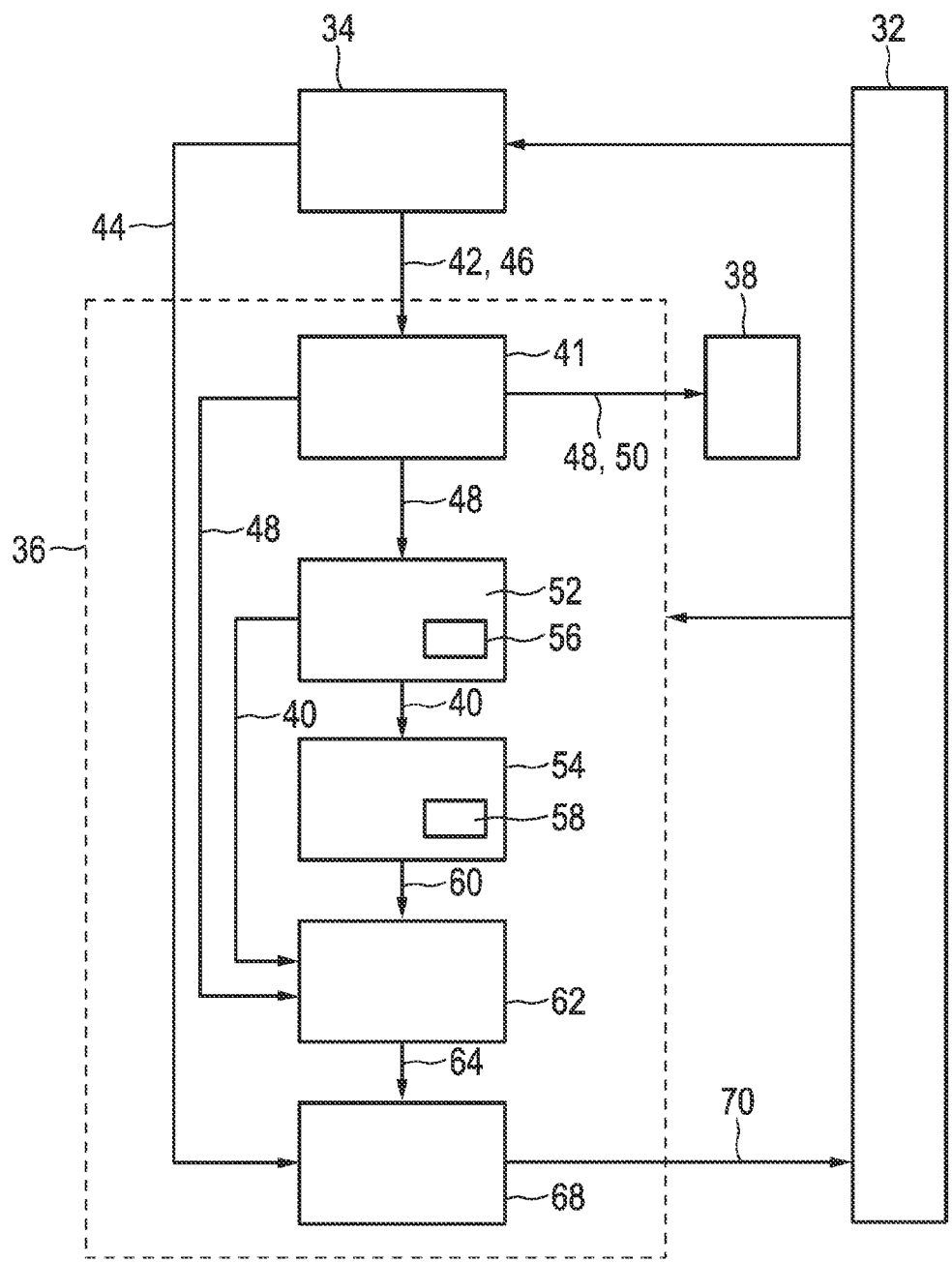
FIG. 4 shows a schematic block diagram of a computed tomography system according to the present invention.

FIG. 3 shows a flow chart of a general embodiment of a method according to the present invention. FIG. 4 shows a schematic block diagram of a processing unit 36 of a computer tomography system 10 according to the present invention. In a first step S10 the acquisition unit acquires a first projection data set 42 (e.g. stored in the storage unit 34), which is reconstructed by a reconstruction unit 41 to obtain a planning image 48. The planning image 48 is used by an identification unit 52 and a selection unit 54. In this embodiment, the identification unit 52 comprises a first user interface 56 and the selection unit 54 comprises a second user interface 58. The planning image 48 is, in this embodiment, shown to a user, e.g. on the display 38. In particular, in step S12, a ROI 40 is identified in the planning image 48 by the identification unit 52, preferably through the first user interface 56. In step S14, a projection angle 60 through the ROI 40 is selected by selection unit 54, preferably through the second user interface 58.

Instead of the first and second user interfaces 56, 58 the identification unit 52 and/or the selection unit 54 may also comprise automatic components, which either suggest a region of interest 40 and/or a projection angle 60, which are shown to the user as suggestion, and/or which are used to refine the ROI 40 and/or the projection angle 60 that were chosen by the user.

Subsequently, in step S16 a calculator 62 determines a target projection value 64 based on the planning image 48, the ROI 40, the projection angle 60, and, preferably, the expected increase in an average intensity of the ROI 40. In one embodiment, the calculator 62 computes the target projection value 64 by computing a line integral through the planning image 48, where the intensities in the ROI 40 have been set to an increased intensity. The integral is performed along the projection 66 (as shown the example of a computed tomography planning image 48 depicted in FIG. 5).

The acquisition unit then (step S18) acquires a second, reduced projection data set 44 (see FIG. 2B), e.g. only one measuring value which corresponds to a projection that goes through the ROI 40 at a selected projection angle 60.

A comparator 68 compares (step S20) projection values from the second projection data set 44 with the target projection value 64 that was computed by the calculator 62. The result of this comparison can be based simply on when an acquired projection value from the second projection data set 44 is larger than the target projection value 64. However, as described before, there can also be more refined comparisons. For example, the condition could be that an acquired projection value from the second projection data set 44 is larger than the target projection value 64 and the projection value acquired at the current time point is higher than the previously acquired projection value. Further refinements could require a minimum slope in the subsequently acquired projection values from the second projection data set 44.

Based on the result 70 of the comparison of the comparator 68, the control unit 32 initiates (step S22) the acquisition of the third projection data set 46 and the reconstruction of the diagnostic image 50 from said third projection data set 46. The diagnostic image 50 is displayed to the user on the display 38.

Figure 5:
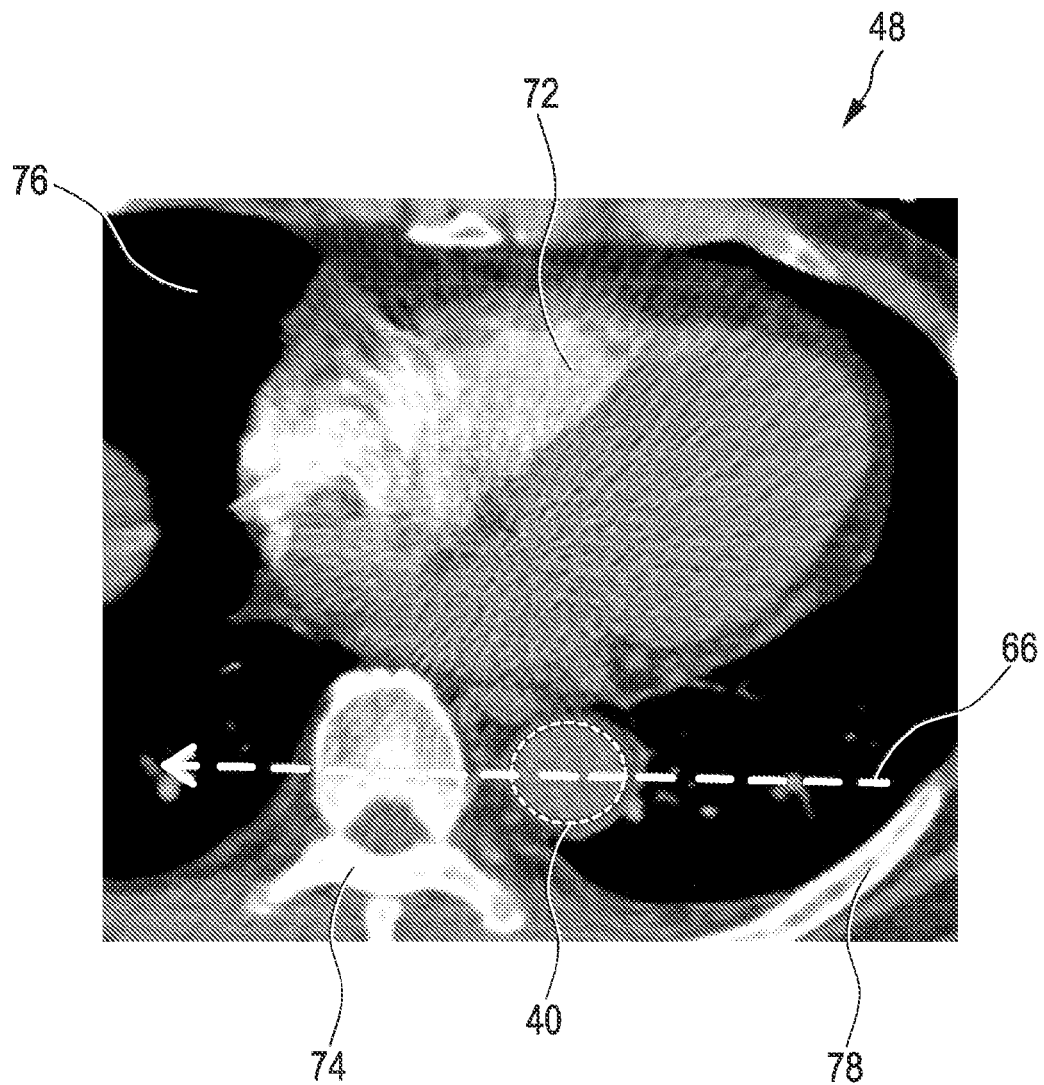
FIG. 5 shows an example of a computed tomography planning image as acquired and reconstructed with a computed tomography system according to the present invention.

FIG. 5 shows an example of a planning image 48 that is used for identifying the ROI 40 and the projection angle. The image shows a cross section of a human thorax. The heart 72, spine 74, part of the lungs 76, and the ribs 78 can be seen. The ROI 40 and the projection 66 (at the particular projection angle) are shown overlaid over the planning image 48, similar to how it could be shown on the first and second user interface 56, 58. It can be seen that the projection 66 goes through the ROI 40 and structures 74, 76, 78, that are not expected to yield uptake of contrast agent.

The present invention enables tracking a bolus or another medium that yields contrast in X-ray imaging. During the tracking phase the computed tomography system 10 according to the present invention minimizes radiation exposure for the patient by acquiring reduced projection data sets 44. Based on a comparison of projection values, which could, e.g., indicate that a bolus has arrived in the target area 40, the acquisition and reconstruction of a diagnostic image 50 is started.

The administration of the bolus or the other contrast medium is typically performed by injection or by swallowing. An injection can be performed for example intravenously, intramuscular, intrathecal or subcutaneous. For examinations of the stomach or the bowels, the administration can be performed simply by swallowing the medium. The bolus or other contrast medium can include any kind of substance that generates a contrast in X-ray images. Its administration can be performed by a physician, a medical assistant, a person of ordinary skill or the patient himself.

The invention can, apart from tracking a bolus of a contrast agent, also be applied for tracking the distribution of other substances in a subject. For instance, it may be use to observe how fast a particular substance, e.g. food or a medicine swallowed by a person, that leads to a sufficient contrast in an image, reaches a particular position in the stomach or the intestine.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A computed tomography system, comprising:
an acquisition unit including an X-ray source and an X-ray detector for acquiring projection data sets,
a reconstruction unit for reconstructing a planning image from a first projection data set with a first projection angle,
an identification unit for identifying a region of interest in the planning image,
a selection unit for selecting a second projection angle through the region of interest and the second projection angle narrows an x-ray beam emitted by the X-ray source relative to the first projection angle,
a calculator for calculating a target projection value for a projection of said region of interest with the selected second projection angle,
a control unit for controlling said acquisition unit to acquire a second, reduced projection data set including projection data from projections of said region of interest with the selected second projection angle, and
a comparator for comparing projection values of the second projection data set with the target projection value, wherein the control unit is adapted to control the acquisition unit to initiate the acquisition of a third projection data set with a third projection angle based on the comparison result and to reconstruct a diagnostic image from the third projection data set.

2. The system of claim 1, wherein the second, reduced projection data set comprises only projection data from projections of said region of interest with the selected projection angle.

3. The system of claim 1, wherein the identification unit comprises a first user interface, which allows a user to identify the region of interest in the planning image.

4. The system of claim 1, wherein the selection unit comprises a second user interface which allows a user to select the second projection angle through the region of interest.

5. The system of claim 4, further comprising a display, wherein the selection unit is adapted for automatically selecting a preferred second projection angle and wherein the display is adapted for displaying said preferred second projection angle.

6. The system of claim 1, wherein the selection unit is adapted for automatically selecting the second projection angle.

7. The system of claim 1, wherein the selection unit is adapted for selecting more than one second projection angle and wherein the second reduced projection data set includes projection data from projections of the identified region of interest with the more than one selected second projection angles.

8. The system of claim 1, wherein the acquisition unit is adapted to acquire the projection values of the second projection data set at subsequent times and the comparator is adapted for computing a rate of change of the projection values acquired at subsequent times.

9. The system of claim 7, wherein the acquisition unit is adapted to acquire the projection values of the second projection data set at subsequent times with equal time intervals in between.

10. The system of claim 1, wherein the acquisition unit further comprises a dynamic collimator for narrowing the X-ray beam emitted from the X-ray source when the second set projection data set is acquired.

11. The system of claim 1, the acquisition unit is adapted to acquire the second projection data set using a grid-switched X-ray source.

12. A method for tracking a bolus in a computed tomography system comprising:
    acquiring a first projection data set at a first projection angle with an acquisition unit and reconstructing a planning image from said first projection data set with a processor,
    identifying a region of interest in the planning image,
    selecting a second projection angle through the region of interest,
    calculating a target projection value for a projection of the region of interest with the selected second projection angle,
    acquiring a second, reduced projection data set including projection data from projections of said region of interest using the selected second projection angle narrowing an X-ray beam emitted by an X-ray source relative to the first projection angle,
    comparing projection values of the second, reduced projection data set with the target projection value, and
    acquiring a third projection data set with a third projection angle and reconstructing a diagnostic image from the third projection data set,
    wherein acquiring the third projection data set is initiated based on the comparison result.

13. A non-transitory computer readable medium comprising a computer program code which when executed cause a computer to control a computed tomography system to perform the following steps:
    acquiring a first projection data set at a first projection angle and reconstructing a planning image from said first projection data set,
    allowing a user to identify a region of interest in the planning image,
    allowing a user to select a second projection angle through the region of interest,
    calculating a target projection value for a projection of the region of interest with the selected second projection angle,
    acquiring a second, reduced projection data set including projection data from projections of said region of interest using the selected second projection angle narrowing an X-ray beam emitted by an X-ray source relative to the first projection angle,
    comparing projection values of the second, reduced projection data set with the target projection value, and
    acquiring a third projection data set at a third projection angle and reconstructing a diagnostic image from the third projection data set,
    wherein acquiring the third projection data set is initiated based on the comparison result.

14. The computed tomography system according to claim 1, wherein the X-ray source includes a collimator arrangement which narrows the X-ray beam.

15. The computed tomography system according to claim 1, wherein the narrowed X-ray beam is detected by one detector element of the X-ray detector.

* * * * *